United States Patent [19]

Puderbaugh

[11] 4,324,260
[45] Apr. 13, 1982

[54] VOLUMETRIC SPIROMETER

[75] Inventor: George Puderbaugh, Manlius, N.Y.

[73] Assignee: Diemolding Corporation, Canastota, N.Y.

[21] Appl. No.: 83,165

[22] Filed: Oct. 9, 1979

[51] Int. Cl.³ .............................................. A61B 5/08
[52] U.S. Cl. ...................................... 128/728; 272/99
[58] Field of Search ........... 128/728, 727, 725, 203.28, 128/204.28, 205.13–205.17; 272/99

[56] References Cited

U.S. PATENT DOCUMENTS

| 3,467,078 | 9/1969 | Bird et al. | 128/728 |
| 3,613,677 | 10/1971 | Blasku | 128/205.16 X |
| 3,621,842 | 11/1971 | Manley | 128/205.16 X |
| 4,096,855 | 6/1978 | Fleury, Jr. | 128/727 X |
| 4,241,740 | 12/1980 | Brown | 128/728 |

FOREIGN PATENT DOCUMENTS

| 848725 | 9/1960 | United Kingdom | 128/205.15 |
| 195037 | 6/1967 | U.S.S.R. | 128/728 |

Primary Examiner—Lee S. Cohen
Attorney, Agent, or Firm—Bruns & Jenney

[57] ABSTRACT

A spirometer for encouraging inhalation exercises and particularly for indicating the volume of air that is inhaled by the user. The spirometer comprises a two-part generally cylindrical housing having a bellows assembly positioned therein. A breathing tube is connected to a port in the housing that communicates with the interior of the bellows. By inhaling through the breathing tube the user causes the bellows to contract and a pointer on the bellows coacts with a scale on the housing to indicate the amount of air that has been inhaled. Each of the housing parts is formed with a plurality of spaced apart discrete wall sections and the sections of the two parts interfit with one another to reduce the size of the spirometer for shipping.

11 Claims, 5 Drawing Figures

VOLUMETRIC SPIROMETER

BACKGROUND OF THE INVENTION

This invention relates generally to medical devices, and has particular reference to a novel volumetric spirometer for encouraging deeper inhalation by post-surgical patients and for measuring the amount of air that is inhaled.

After chest surgery, it is frequently very painful for the patient to breathe and, in addition, the patient may be so weakened that breathing is difficult. In such cases, the patient tends to breathe shallowly and deeper inhalation must be encouraged to help prevent lung congestion which can lead to pneumonia. Deeper breathing also helps to recondition muscles and aids in the healing process.

Lung exercising devices and spirometers of various types have been developed heretofore both for medical use as noted above and for non-medical uses such as improving breath control for singing or playing a musical instrument. Many of these devices, however, are unduly complex or cumbersome and some are relatively expensive to manufacture. A relatively simple device is the incentive spirometer disclosed in U.S. Pat. No. 4,096,855, issued June 27, 1978 to G. J. Fleury, Jr., and this is the closest prior art known to the applicant. The present invention differs from the Fleury spirometer inter alia in its novel bellows arrangement and novel interfitting side wall construction as will be explained more fully hereinafter.

SUMMARY OF THE INVENTION

The volumetric spirometer of the instant invention comprises a housing having upper and lower, generally cylindrical mating sections and a bellows assembly positioned in the housing. The bellows assembly includes a sleeve of flexible polymeric material having a helical wire spring incorporated therein and a bottom closure for the sleeve. The upper end of the bellows sleeve is secured in sealed relation to the top of the upper housing section and a port in the latter communicates with the interior of the bellows. A breathing tube is connected to the port and by inhaling through it the user causes the bellows to contract. A pointer on the bellows coacts with a scale on the housing to indicate the amount of air that has been inhaled.

The upper and lower mating sections of the housing are each formed with a plurality of spaced apart discrete wall portions. These portions are generally rectangular and each adjacent pair of portions is separated by an open space having approximately the same dimensions. This permits the wall portions of one housing section to be positioned in the open spaces of the other section to reduce the size of the spirometer for shipping. The spirometer is set up for use by withdrawing the wall portions from the spaces and rotating one housing section relative to the other to bring the free ends of the wall portions of the respective sections into confronting, abutting relation with one another. Means are provided for securing the housing sections together in this position.

DESCRIPTION OF THE PREFERRED EMBODIMENT

Figure 2:
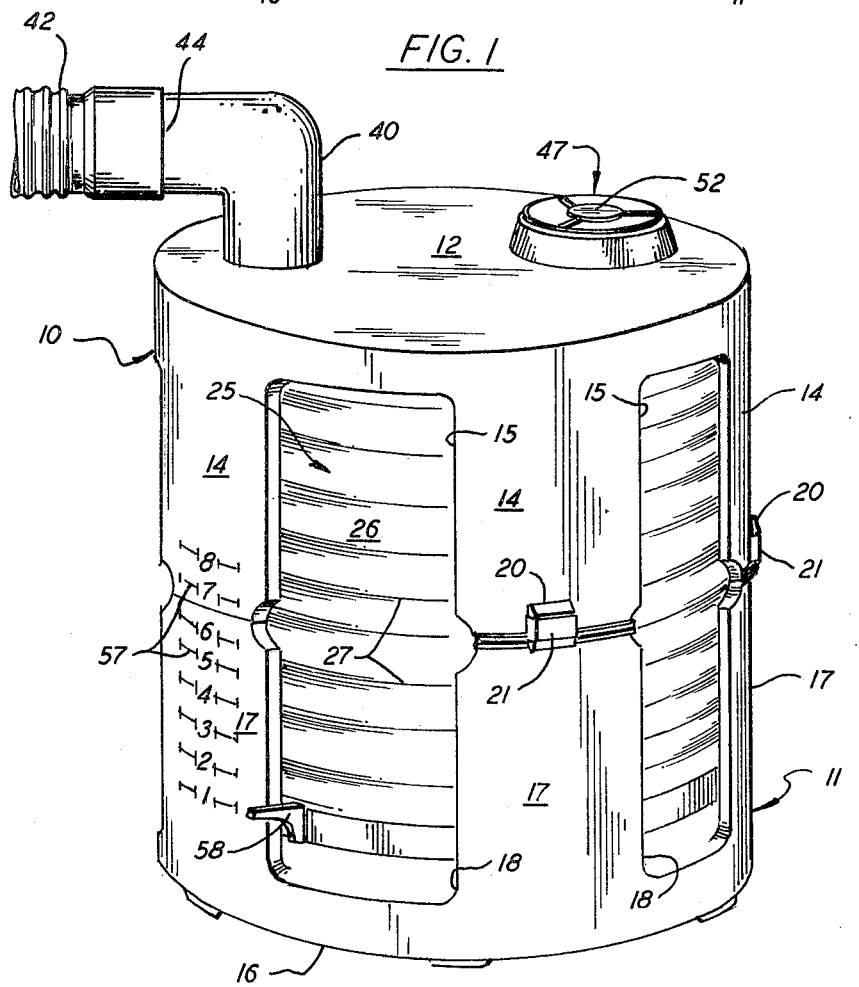
FIG. 2 is a top perspective view of the spirometer of FIG. 1 shown set up for use.
Figure 4:
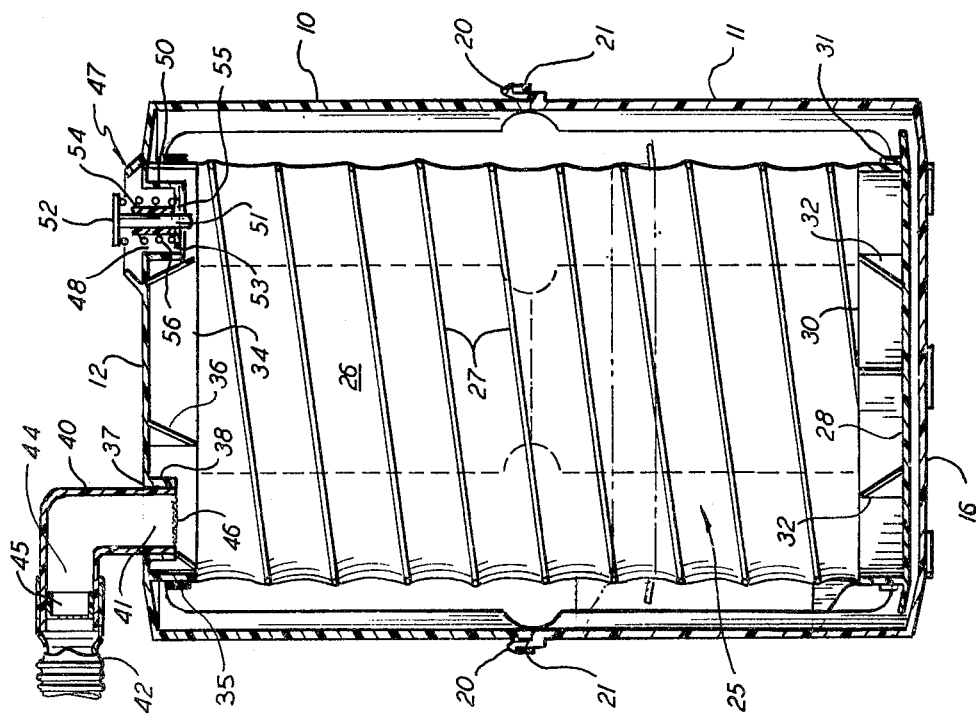
FIG. 4 is a vertical sectional view taken on line 4—4 of FIG. 3.
Figure 3:
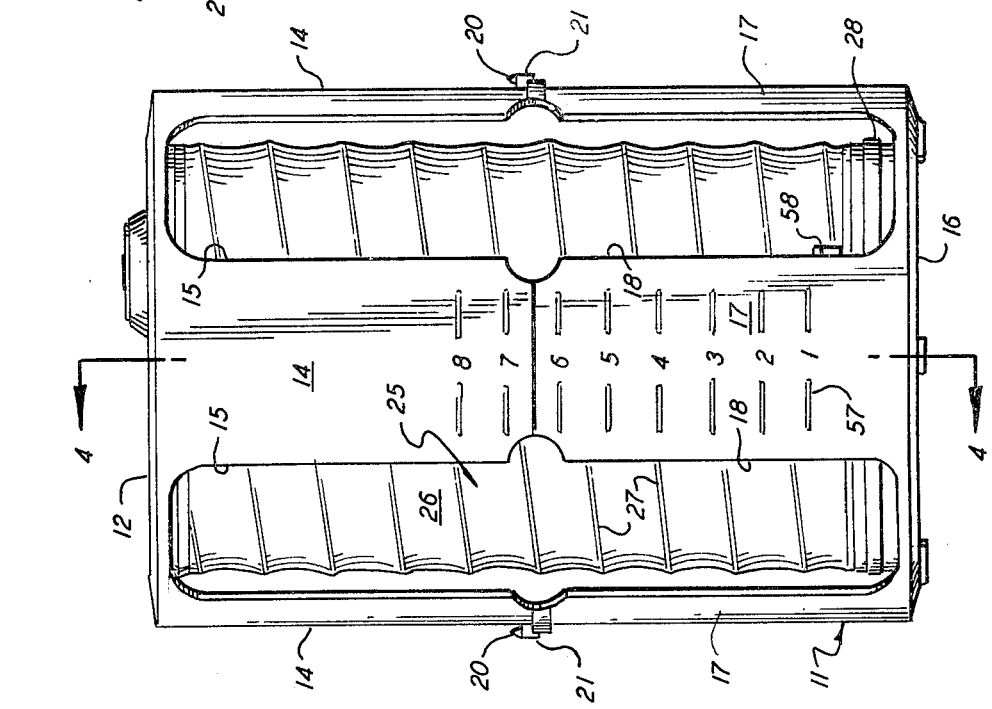
FIG. 3 is an enlarged front elevation of the spirometer.

Referring now to the drawings, and with particular reference to FIGS. 2-4, the volumetric spirometer comprises a generally cylindrical housing having mating upper and lower sections 10 and 11, respectively. Upper housing section 10 has a flat top wall 12 and its cylindrical side wall is formed with a plurality of discrete rectangular wall portions 14 all of the same size. Adjacent wall portions 14 are separated by rectangular open spaces 15 all of which are also of the same size. Similarly, the lower housing section 11 has a flat bottom wall 16 and its cylindrical side wall is formed with a plurality of alternate rectangular wall portions 17 and open spaces 18 having the same dimensions as wall portions 14 and spaces 15.

Figure 1:
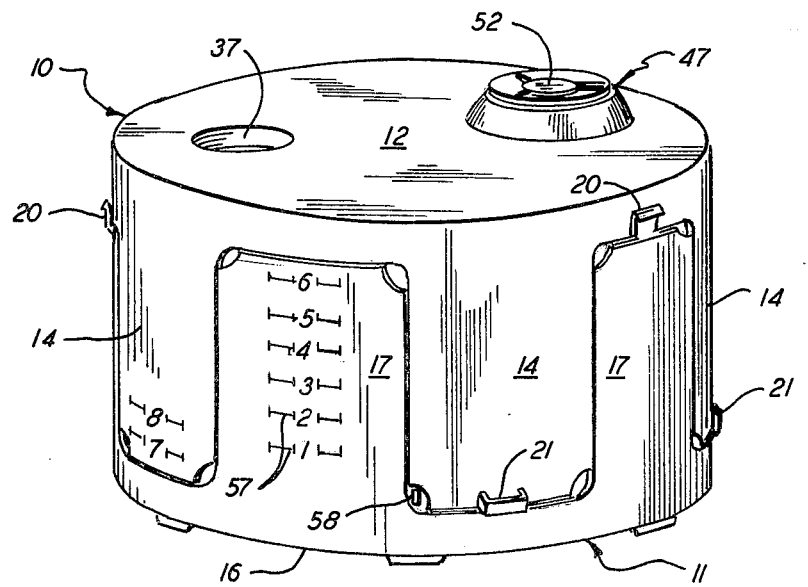
FIG. 1 is a top perspective view of a volumetric spirometer embodying the invention with the upper and lower housing sections interfitted for shipping.

The spaces 15 and 18 are slightly larger than the wall portions 14 and 17 which permits the spaces of each housing section to receive with a sliding fit the wall portions of the other section as is shown in FIG. 1. This is the way the spirometer is assembled for shipping and storage and by comparison with FIG. 2, showing the spirometer set up for use, it can be seen that the height of the device is reduced by almost one half.

Figure 5:
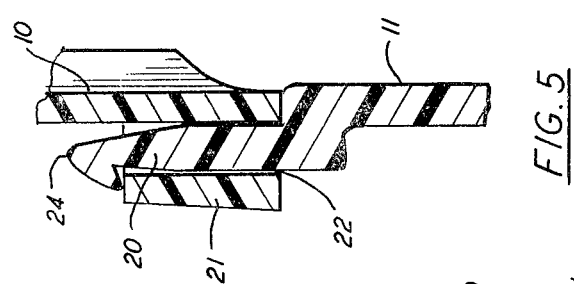
FIG. 5 is a greatly enlarged sectional view through the securing means for the housing sections.

When the spirometer is to be readied for use, its outer packaging (not shown) is removed, the upper and lower housing sections 10 and 11 are separated and one section is rotated relative to the other to bring the free ends of the wall portions 14, 17 into confronting, abutting relation as shown in FIGS. 2-4. The housing sections are maintained in this position by locking means consisting of coacting hooks 20 and straps 21, FIG. 5. There are at least two sets of such hooks and straps with the hooks being formed integrally with the wall portions 17 of the lower housing section and the straps being formed integrally with the upper section wall portions 14. In assembling the sections, upper section 10 is pushed down into engagement with lower section 11 which causes the lower inner edges 22, FIG. 5, of the straps 21 to engage the cam surfaces 24 on the hooks 20 and spring the latter radially inwardly after which they spring back outwardly into locking position as shown.

Positioned inside the spirometer housing is a bellows member or assembly generally indicated at 25. The bellows comprises a flexible sleeve 26 of a polymeric material such as vinyl or polyester in which a helical wire spring 27 is incorporated, the sleeve and spring combination being a commercially available product. The bellows includes a bottom closure in the form of a circular plate 28, FIG. 4, having an upstanding circular flange 30. The lower end of sleeve 26 encircles this flange and is held in sealed relation thereto by an outer clamping ring 31. The flange 30 is reinforced by a plurality of radially disposed interior ribs 32 as shown.

The top wall 12 of the upper housing section 10 has an integral circular flange 34, FIG. 4, which depends from its inner surface. This flange is encircled by the upper end of bellows sleeve 26, the sleeve being maintained in sealed relation to the flange by a clamping ring 35. Flange 34 is also reinforced by a plurality of radially disposed ribs 36.

The upper housing section top wall 12 is formed with a circular port 37, FIG. 4, having a depending interior flange 38. This port communicates with the interior of the bellows 25 and when the spirometer is being readied for use an elbow 40 is inserted in the port, the inner end 41 of the elbow being formed with a locking taper that engages the flange 38. A conventional flexible breathing or inhalation tube 42 is releasably connected at one end to the outer end 44 of the elbow, the tube having the usual mouthpiece (not shown) at its other end. The elbow is provided with a check valve 45 for purposes to be described and also with a screen filter cap 46.

The housing top wall 12 is also provided with a normally closed valve 47, FIG. 4, located in a circular port 48 having a depending interior flange 50. The valve includes a stem 51 with a push button 52 at its top and a circular plate 53 at its bottom. The plate normally engages the lower edge of flange 50 to close the port 48 and to this end is provided with suitable gasket material on its upper surface. The valve stem 51 is supported by and is slidably movable in a sleeve 54 that is rigidly connected at its lower end to the flange 50 by a plurality of angularly spaced radial spokes 55. A compression spring 56 that is positioned between the spokes and the push button 52 normally holds the valve in closed position.

The bellows spring 27 is calibrated so that its spring constant in extended position supports the closure plate 28 just above the bottom wall 16 of the lower housing section. This means that when a user inhales through the breathing tube 42 causing a reduction of pressure in the bellows, this reduction in interior pressure is assisted by the spring in raising the bottom plate and contracting the bellows. With this arrangement, it is relatively easy to start to lift the plate but the higher the plate moves the more difficult the task becomes because the spring does less and less work. This enables patients with all degrees of strength to benefit from the spirometer.

To provide a visual indication of the volume of air that is being inhaled by a user, one pair of mating wall portions 14,17 can be provided with a scale 57, FIG. 3, which coacts with a pointer 58 attached to the bellows closure plate 28, FIGS. 1 and 2. The pointer moves upwardly with the plate when the user inhales and measures the volume of air inhaled in cubic centimeters or milliliters.

In operation, after the user has inhaled as deeply as he can the elevated closure plate 28 will remain in the position to which it has been raised because the check valve 45, FIG. 4, will not permit air to re-enter the bellows interior. This is advantageous because it facilitates reading the scale, and having the user exhale into the bellows is not desired. After reading the scale, fresh air can be admitted into the bellows by depressing the push button 52 of valve 47.

The valve 47 can also operate as a relief valve. Thus, its spring 56 is calibrated so that if the closure plate 28 is brought way up into the upper section of the housing, the outside, ambient pressure will cause the valve to open and air to enter the bellows. This prevents overexertion by the user which could possibly result in pneumothorax.

From the foregoing description, it will be apparent that the invention provides a novel and very advantageous spirometer construction. As will be understood by those familiar with the art, the invention may be embodied in other specific forms without departing from the spirit or essential characteristics thereof.

I claim:

1. A volumetric spirometer comprising a generally cylindrical two-part housing having top and bottom walls, a bellows member positioned in the housing, the bellows member having a bottom closure and being suspended in extended condition from the housing top wall, and port means in the top wall in communication with the interior of the bellows member whereby removing air from the bellows member interior through the port means causes the bellows member to contract, each of the housing parts having a plurality of spaced apart discrete wall sections, the wall sections of the two parts interfitting with one another to reduce the size of the spirometer for shipping, the wall sections of the housing parts being brought into confronting, abutting relation when the spirometer is set up for use.

2. A spirometer as defined in claim 1 wherein the bellows member is a substantially cylindrical flexible sleeve having a helical spring incorporated therein.

3. A spirometer as defined in claim 1 wherein the wall sections of the housing parts are generally rectangular and each adjacent pair of sections is separated by an open space of approximately the same dimensions whereby the spaces in one housing part receive the wall sections of the other housing part when the two parts are interfitted for shipping.

4. A volumetric spirometer comprising a generally cylindrical housing having top and bottom walls, a bellows member positioned in the housing, the bellows member comprising a flexible sleeve having a helical spring incorporated therein, the bellows member having a bottom closure and being suspended in extended condition from the housing top wall, the bellows member spring being calibrated so that its spring constant in extended condition supports the bottom closure just above the bottom wall of the housing, and port means in the top wall in communication with the interior of the bellows member whereby removing air from the bellows member interior through the port causes the bellows member to contract and its bottom closure to move toward the top wall of the housing.

5. A spirometer as defined in claim 4 together with a breathing tube connected in sealed manner to said port means whereby a user of the spirometer can inhale through the tube and cause the bottom closure of the bellows member to move upwardly towards the top wall of the housing, and coacting means on the bottom closure and the housing to indicate the volume of air inhaled by the user.

6. A volumetric spirometer comprising a housing having upper and lower generally cylindrical mating sections, the upper section having a top wall and the lower section having a bottom wall, a bellows assembly positioned in the housing, the bellows assembly including a substantially cylindrical flexible sleeve having a helical spring incorporated therein, a bottom closure secured to the bellows assembly sleeve, the upper end of the bellows assembly sleeve being secured in sealed relation to the upper section top wall whereby the bellows assembly is suspended therefrom with its bottom closure spaced above the bottom wall of the lower section, the bellows assembly spring being calibrated so that its spring constant in extended condition supports the bottom closure just above the bottom wall of the lower section, and port means in the upper section top wall in communication with the interior of the bellows assembly whereby removing air from the bellows assembly interior through the port means causes the bellows assembly to contract and its bottom closure to move upwardly in the housing toward the upper section top wall.

7. A spirometer as defined in claim 6 together with a breathing tube connected in sealed manner to said port means whereby a user of the spirometer can inhale through the tube and remove air from the bellows assembly interior, and coacting means on the bottom closure and the housing to indicate the volume of air inhaled by the user.

8. A spirometer as defined in claim 7 wherein the breathing tube includes a check valve that prevents the user from exhaling air back into the bellows assembly interior.

9. A spirometer as defined in claim 6 wherein each of the upper and lower mating sections of the housing is formed with a plurality of spaced apart discrete wall portions, the wall portions of the two sections interfitting with one another to reduce the size of the spirometer for shipping, the wall portions of the sections being brought into confronting, abutting relation when the spirometer is set up for use.

10. A spirometer as defined in claim 9 wherein wall portions of the housing sections are generally rectangular and each adjacent pair of portions is separated by an open space having approximately the same dimensions, the spaces in one housing section receiving the wall portions of the other housing section when the two sections are interfitted for shipping, the bellows assembly being in contracted condition within the sections.

11. A spirometer as defined in claim 9 together with coacting means on the upper and lower housing sections to secure them together when the spirometer is set up for use.

* * * * *